United States Patent
Clausen

(10) Patent No.: US 9,707,104 B2
(45) Date of Patent: Jul. 18, 2017

(54) PROSTHETIC ANKLE AND METHOD OF CONTROLLING SAME BASED ON ADAPTATION TO SPEED

(71) Applicant: Ossur hf, Reykjavik (IS)

(72) Inventor: Arinbjorn Clausen, Reykjavik (IS)

(73) Assignee: Össur hf, Reykjavik (IS)

(\*) Notice: Subject to any disclaimer, the term of this patent is extended or adjusted under 35 U.S.C. 154(b) by 0 days.

(21) Appl. No.: 14/206,956

(22) Filed: Mar. 12, 2014

(65) Prior Publication Data

US 2014/0277586 A1 Sep. 18, 2014

Related U.S. Application Data

(60) Provisional application No. 61/785,248, filed on Mar. 14, 2013.

(51) Int. Cl.
*A61F 2/70* (2006.01)
*A61F 2/76* (2006.01)
(Continued)

(52) U.S. Cl.
CPC .............. *A61F 2/68* (2013.01); *A61F 2/6607* (2013.01); *A61F 2/644* (2013.01); *A61F 2002/5003* (2013.01); *A61F 2002/5018* (2013.01); *A61F 2002/701* (2013.01); *A61F 2002/704* (2013.01); *A61F 2002/74* (2013.01);
(Continued)

(58) Field of Classification Search
CPC .. A61F 2/60; A61F 2/66; A61F 2/6607; A61F 2/68; A61F 2/76
See application file for complete search history.

(56) References Cited

U.S. PATENT DOCUMENTS

| 909,859 A | 1/1909 | Apgar |
|---|---|---|
| 2,475,373 A | 7/1949 | Catranis |

(Continued)

FOREIGN PATENT DOCUMENTS

| CH | 543277 | 12/1973 |
|---|---|---|
| CN | 2043873 | 9/1989 |

(Continued)

OTHER PUBLICATIONS

Dietl et al., "Der Einsatz von Elektronik bei Prothesen zur Versorgung der unteren Extremität," Med. Orth. Tech. , 1997, vol. 117, pp. 31-35.

(Continued)

*Primary Examiner* — Marcia Watkins
(74) *Attorney, Agent, or Firm* — Knobbe, Martens, Olson & Bear, LLP

(57) ABSTRACT

Prosthetic devices and methods of controlling the same are provided. A prosthetic ankle device includes a foot unit and lower limb member moveable relative to one another and defining an ankle angle therebetween. The prosthetic ankle device further includes a controller to operate the device using different ankle angles depending on, for example, a user's gait speed. Methods of controlling the prosthetic ankle device include operating the device at different ankle angles depending on gait speed. For example, the prosthetic ankle device can provide for relatively more dorsiflexion at relatively slower gait speeds and relatively more plantarflexion at relatively faster gait speeds.

21 Claims, 10 Drawing Sheets

(51) Int. Cl.
  *A61F 2/66* (2006.01)
  *A61F 2/64* (2006.01)
  *A61F 2/68* (2006.01)
  *A61F 2/50* (2006.01)
  *A61F 2/74* (2006.01)

(52) U.S. Cl.
  CPC . *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | |
|---|---|---|
| 2,568,051 A | 9/1951 | Catranis |
| 3,589,134 A | 6/1971 | Hackmann |
| 3,871,032 A | 3/1975 | Karas |
| 3,953,900 A | 5/1976 | Thompson |
| 4,030,141 A | 6/1977 | Graupe |
| 4,209,860 A | 7/1980 | Graupe |
| 4,387,472 A | 6/1983 | Wilson |
| 4,579,558 A | 4/1986 | Ramer |
| 4,652,266 A | 3/1987 | Truesdell |
| 4,776,852 A | 10/1988 | Bubic |
| 4,805,455 A | 2/1989 | DelGiorno et al. |
| 5,020,790 A | 6/1991 | Beard et al. |
| 5,062,673 A | 11/1991 | Mimura |
| 5,201,772 A | 4/1993 | Maxwell |
| 5,246,465 A | 9/1993 | Rincoe et al. |
| 5,252,102 A | 10/1993 | Singer et al. |
| 5,252,901 A | 10/1993 | Ozawa et al. |
| 5,282,460 A | 2/1994 | Boldt |
| 5,376,138 A | 12/1994 | Bouchard et al. |
| 5,376,141 A | 12/1994 | Phillips |
| 5,383,939 A | 1/1995 | James |
| 5,413,611 A | 5/1995 | Haslam, II et al. |
| 5,443,528 A | 8/1995 | Allen |
| 5,455,497 A | 10/1995 | Hirose et al. |
| 5,484,389 A | 1/1996 | Stark et al. |
| 5,571,205 A | 11/1996 | James |
| 5,650,704 A | 7/1997 | Pratt et al. |
| 5,662,693 A | 9/1997 | Johnson et al. |
| 5,695,527 A | 12/1997 | Allen |
| 5,888,212 A | 3/1999 | Petrofsky et al. |
| 5,888,213 A | 3/1999 | Sears et al. |
| 5,893,891 A | 4/1999 | Zahedi |
| 5,929,332 A | 7/1999 | Brown |
| 5,948,021 A | 9/1999 | Radcliffe |
| 5,954,621 A | 9/1999 | Joutras et al. |
| 5,957,981 A | 9/1999 | Gramnas |
| 5,984,972 A | 11/1999 | Huston et al. |
| 6,061,577 A | 5/2000 | Andrieu et al. |
| 6,086,616 A | 7/2000 | Okuda et al. |
| 6,091,977 A | 7/2000 | Tarjan et al. |
| 6,187,052 B1 | 2/2001 | Molino et al. |
| 6,206,932 B1 | 3/2001 | Johnson |
| 6,378,190 B2 | 4/2002 | Akeel |
| 6,379,393 B1 | 4/2002 | Mavroidis et al. |
| 6,423,098 B1 | 7/2002 | Biedermann |
| 6,436,149 B1 | 8/2002 | Rincoe |
| 6,443,993 B1 | 9/2002 | Koniuk |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,543,987 B2 | 4/2003 | Ehrat |
| 6,587,728 B2 | 7/2003 | Fang et al. |
| 6,610,101 B2 | 8/2003 | Herr et al. |
| 6,613,097 B1 | 9/2003 | Cooper |
| 6,645,252 B2 | 11/2003 | Asai et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,813,582 B2 | 11/2004 | Levi et al. |
| 6,824,569 B2 | 11/2004 | Okediji |
| 6,875,241 B2 | 4/2005 | Christensen |
| 6,908,488 B2 | 6/2005 | Passivaara et al. |
| 6,910,331 B2 | 6/2005 | Asai et al. |
| 6,955,692 B2 | 10/2005 | Grundei |
| 6,966,882 B2 | 11/2005 | Horst |
| 7,029,500 B2 | 4/2006 | Martin |
| 7,066,964 B2 | 6/2006 | Wild |
| 7,118,601 B2 | 10/2006 | Yasui |
| 7,137,998 B2 | 11/2006 | Bédard et al. |
| 7,147,667 B2 | 12/2006 | Bédard et al. |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,209,788 B2 | 4/2007 | Nicolelis et al. |
| 7,279,009 B2 | 10/2007 | Herr et al. |
| 7,300,240 B2 | 11/2007 | Brogardh |
| 7,308,333 B2 | 12/2007 | Kern et al. |
| 7,313,463 B2 | 12/2007 | Herr et al. |
| 7,314,490 B2 | 1/2008 | Bédard et al. |
| 7,381,192 B2 | 6/2008 | Brodard et al. |
| 7,410,471 B1 | 8/2008 | Campbell et al. |
| 7,455,696 B2 | 11/2008 | Bisbee, III et al. |
| 7,485,152 B2 | 2/2009 | Haynes et al. |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,578,799 B2 | 8/2009 | Thorsteinsson et al. |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bédard et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bédard et al. |
| 7,867,284 B2 | 1/2011 | Bédard et al. |
| 7,918,808 B2 | 4/2011 | Simmons |
| 7,942,935 B2 | 5/2011 | Iversen et al. |
| 7,955,398 B2 | 6/2011 | Bédard et al. |
| 7,992,849 B2 | 8/2011 | Sugar et al. |
| 8,048,007 B2 | 11/2011 | Roy |
| 8,048,172 B2 | 11/2011 | Jonsson et al. |
| 8,057,550 B2 | 11/2011 | Clausen et al. |
| 8,075,633 B2 | 12/2011 | Herr et al. |
| 8,083,807 B2 | 12/2011 | Auberger et al. |
| 8,109,890 B2 | 2/2012 | Kamiar et al. |
| 8,142,370 B2 | 3/2012 | Weinberg et al. |
| 8,231,687 B2 | 7/2012 | Bédard et al. |
| 8,323,354 B2 | 12/2012 | Bédard et al. |
| 8,366,788 B2 | 2/2013 | Moser et al. |
| 8,403,997 B2 | 3/2013 | Sykes et al. |
| 8,435,309 B2 | 5/2013 | Gilbert et al. |
| 8,500,823 B2 | 8/2013 | Herr et al. |
| 8,512,415 B2 | 8/2013 | Herr et al. |
| 8,551,184 B1 | 10/2013 | Herr |
| 7,431,737 C1 | 12/2013 | Ragnarsdottir et al. |
| 8,601,897 B2 | 12/2013 | Lauzier et al. |
| 8,617,254 B2 | 12/2013 | Bisbee, III et al. |
| 8,652,218 B2 | 2/2014 | Goldfarb et al. |
| 8,657,886 B2 | 2/2014 | Clausen et al. |
| 8,702,811 B2 | 4/2014 | Ragnarsdottir et al. |
| 7,896,927 C1 | 5/2014 | Clausen et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,870,967 B2 | 10/2014 | Herr et al. |
| 8,986,397 B2 | 3/2015 | Bédard et al. |
| 9,044,346 B2 | 6/2015 | Langlois et al. |
| 9,060,884 B2 | 6/2015 | Langlois |

(56) References Cited

U.S. PATENT DOCUMENTS

| | | |
|---|---|---|
| 9,066,819 B2 | 6/2015 | Gramnaes |
| 9,078,774 B2 | 7/2015 | Jonsson et al. |
| 9,114,029 B2 | 8/2015 | Ásgeirsson |
| 9,271,851 B2 | 3/2016 | Claussen et al. |
| 9,345,591 B2 | 5/2016 | Bisbee, III et al. |
| 9,358,137 B2 | 6/2016 | Bédard et al. |
| 9,526,635 B2 | 12/2016 | Gilbert et al. |
| 9,526,636 B2 | 12/2016 | Bédard et al. |
| 2001/0002772 A1 | 6/2001 | Kim et al. |
| 2002/0007690 A1 | 1/2002 | Song et al. |
| 2002/0079857 A1 | 6/2002 | Ishii et al. |
| 2004/0054423 A1* | 3/2004 | Martin .................. 623/25 |
| 2004/0064195 A1 | 4/2004 | Herr |
| 2004/0078299 A1 | 4/2004 | Down-Logan et al. |
| 2004/0153484 A1 | 8/2004 | Unno |
| 2004/0217324 A1 | 11/2004 | Hsu et al. |
| 2005/0049719 A1 | 3/2005 | Wilson |
| 2005/0070834 A1 | 3/2005 | Herr et al. |
| 2005/0071017 A1 | 3/2005 | Lecomte et al. |
| 2005/0107889 A1 | 5/2005 | Bédard et al. |
| 2005/0113973 A1 | 5/2005 | Endo et al. |
| 2005/0137717 A1 | 6/2005 | Gramnaes |
| 2005/0166685 A1 | 8/2005 | Boiten |
| 2005/0216097 A1 | 9/2005 | Rifkin |
| 2005/0283257 A1 | 12/2005 | Bisbee et al. |
| 2006/0069336 A1 | 3/2006 | Krebs et al. |
| 2006/0184280 A1 | 8/2006 | Oddsson et al. |
| 2006/0189899 A1 | 8/2006 | Flaherty et al. |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0043449 A1 | 2/2007 | Herr et al. |
| 2007/0061016 A1 | 3/2007 | Kuo et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2008/0004718 A1 | 1/2008 | Mosler |
| 2008/0046096 A1 | 2/2008 | Bédard et al. |
| 2008/0058668 A1 | 3/2008 | Seyed Momen et al. |
| 2008/0141813 A1 | 6/2008 | Ehrat |
| 2008/0262635 A1 | 10/2008 | Moser et al. |
| 2008/0300692 A1* | 12/2008 | Moser et al. ............ 623/55 |
| 2008/0306612 A1 | 12/2008 | Mosler |
| 2009/0088912 A1 | 4/2009 | Rajaraman |
| 2009/0192625 A1 | 7/2009 | Boiten |
| 2009/0222105 A1* | 9/2009 | Clausen .................. 623/27 |
| 2010/0023133 A1 | 1/2010 | Fairbanks et al. |
| 2010/0030343 A1 | 2/2010 | Hansen et al. |
| 2010/0042228 A1 | 2/2010 | Doddroe et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0185301 A1 | 7/2010 | Hansen et al. |
| 2010/0241242 A1 | 9/2010 | Herr et al. |
| 2010/0262260 A1 | 10/2010 | Bédard et al. |
| 2010/0275718 A1 | 11/2010 | Stuart et al. |
| 2010/0324456 A1 | 12/2010 | Jónsson et al. |
| 2010/0324699 A1 | 12/2010 | Herr et al. |
| 2011/0015761 A1 | 1/2011 | Celebi et al. |
| 2011/0106274 A1 | 5/2011 | Ragnarsdottir et al. |
| 2011/0125290 A1 | 5/2011 | Langlois |
| 2011/0130847 A1 | 6/2011 | Bédard et al. |
| 2011/0132131 A1 | 6/2011 | Worz |
| 2011/0137429 A1 | 6/2011 | Bédard et al. |
| 2011/0196509 A1 | 8/2011 | Jansent et al. |
| 2011/0202144 A1 | 8/2011 | Palmer et al. |
| 2011/0208322 A1 | 8/2011 | Rifkin et al. |
| 2011/0224804 A1 | 9/2011 | Clausen et al. |
| 2011/0295384 A1 | 12/2011 | Herr et al. |
| 2012/0016492 A1 | 1/2012 | Clausen |
| 2012/0078415 A1 | 3/2012 | Kubo et al. |
| 2012/0130508 A1 | 5/2012 | Harris et al. |
| 2012/0191221 A1 | 7/2012 | Bédard et al. |
| 2012/0209405 A1 | 8/2012 | Herr et al. |
| 2012/0283844 A1 | 11/2012 | Langlois |
| 2012/0283845 A1 | 11/2012 | Herr et al. |
| 2013/0035769 A1 | 2/2013 | Bédard et al. |
| 2013/0118287 A1 | 5/2013 | Holgate |
| 2013/0142608 A1 | 6/2013 | Zhang et al. |
| 2013/0144402 A1 | 6/2013 | Clausen et al. |
| 2013/0173022 A1 | 7/2013 | Arabian et al. |
| 2013/0204395 A1 | 8/2013 | Gramnaes |
| 2013/0218295 A1 | 8/2013 | Holgate et al. |
| 2013/0268093 A1 | 10/2013 | Gilbert et al. |
| 2013/0297041 A1 | 11/2013 | Bédard et al. |
| 2014/0074243 A1 | 3/2014 | Holgate |
| 2014/0081424 A1 | 3/2014 | Herr et al. |
| 2014/0114437 A1 | 4/2014 | Herr et al. |
| 2014/0121782 A1 | 5/2014 | Herr et al. |
| 2014/0156025 A1 | 6/2014 | Bisbee, III et al. |
| 2014/0200680 A1 | 7/2014 | Holgate et al. |
| 2014/0243997 A1 | 8/2014 | Clausen et al. |
| 2014/0330393 A1 | 11/2014 | Ward et al. |
| 2015/0032225 A1 | 1/2015 | Oddsson et al. |
| 2015/0073566 A1 | 3/2015 | Ragnarsdottir et al. |
| 2015/0164661 A1 | 6/2015 | Ragnarsdottir et al. |
| 2015/0223952 A1 | 8/2015 | Langlois et al. |
| 2015/0265429 A1 | 9/2015 | Jónsson et al. |
| 2015/0297368 A1 | 10/2015 | Langlois |
| 2015/0320573 A1 | 11/2015 | Gramnaes |
| 2015/0328020 A1 | 11/2015 | Clausen et al. |
| 2016/0302956 A1 | 10/2016 | Gilbert et al. |

FOREIGN PATENT DOCUMENTS

| | | |
|---|---|---|
| CN | 2043873 U | 9/1989 |
| CN | 1215614 | 5/1999 |
| CN | 2400072 Y | 10/2000 |
| DE | 43 05 213 | 8/1993 |
| DE | 42 29 330 | 3/1994 |
| EP | 0 358 056 | 3/1990 |
| EP | 0 380 060 | 8/1990 |
| EP | 1 169 982 | 1/2002 |
| EP | 1 410 780 | 4/2004 |
| EP | 1 442 704 | 8/2004 |
| EP | 1 547 567 | 6/2005 |
| EP | 1 792 597 | 6/2007 |
| EP | 2 702 963 | 3/2014 |
| FR | 2 816 463 | 5/2002 |
| GB | 2 201 260 | 8/1988 |
| GB | 2 260 495 | 4/1993 |
| GB | 2 301 776 | 12/1996 |
| GB | 2 302 949 | 2/1997 |
| GB | 2 367 753 | 4/2002 |
| JP | 59-032453 | 2/1984 |
| JP | 59-071747 | 4/1984 |
| JP | 59-088147 | 5/1984 |
| JP | 59-189843 | 10/1984 |
| JP | 60-177102 | 9/1985 |
| JP | 05-123348 | 5/1993 |
| JP | 05-161668 | 6/1993 |
| JP | 07-024766 | 1/1995 |
| JP | 11-215793 | 8/1999 |
| JP | 2002-191654 | 7/2002 |
| JP | 2005-500 | 1/2005 |
| JP | 2005-536317 | 12/2005 |
| JP | 2009-153660 | 7/2009 |
| KR | 2002-0041137 | 6/2002 |
| SU | 1447366 | 12/1988 |
| SU | 1731210 | 5/1992 |
| WO | WO 94/09727 | 5/1994 |
| WO | WO 96/41599 | 12/1996 |
| WO | WO 97/27822 | 8/1997 |
| WO | WO 00/27318 | 5/2000 |
| WO | WO 03/003953 | 1/2003 |
| WO | WO 03/088373 | 10/2003 |
| WO | WO 2004/017890 | 3/2004 |
| WO | WO 2006/076164 | 7/2006 |
| WO | WO 2007/025116 | 3/2007 |
| WO | WO 2008/080231 | 7/2008 |
| WO | WO 2010/027968 | 3/2010 |
| WO | WO 2011/005482 | 1/2011 |

(56) References Cited

FOREIGN PATENT DOCUMENTS

| WO | WO 2011/096965 | 8/2011 |
|---|---|---|
| WO | WO 2013/006585 | 1/2013 |
| WO | WO 2013/0148726 | 10/2013 |
| WO | WO 2014/133975 | 9/2014 |
| WO | WO 2014/159114 | 10/2014 |
| WO | WO 2015/157723 | 10/2015 |

OTHER PUBLICATIONS

DIGINFO TV, "Powered Prosthetic Thigh and Leg", uploaded Nov. 7, 2008 http://www.youtube.com/watch?v=lqjtTzNEd54&feature=youtu.be%3E [Screenshots retrieved Oct. 23, 2014 in 9 pages].

"Extension Spring Design Theory, Spring Rate of Extension Springs," http://web.archive.org/web/20131209120508/http://springipedia.com/extension-design-theory.asp as archived Dec. 9, 2013 in 1 page.

Herr et al., "Patient-Adaptive Prosthetic and Orthotic Leg Systems," In Proceedings of the 12th Nordic Baltic Conference on Biomedical Engineering and Medical Physics, Jun. 18-22, 2002, pp. 18-21.

Aug. 27, 2014 International Search Report and Written Opinion for International Application No. PCT/US14/22013 filed on Mar. 7, 2014.

"The Electronic C-Leg® Knee Joint System," Instructions for Use, Otto Bock®, 2002, pp. 30. http://www.ottobockus.com/products/lower_limb_prosthetics/c-leg_instructions.pdg (printed Jul. 20, 2006).

Aminian et al., "Estimation of Speed and Incline of Walking Using Neural Network," IEEE Transactions on Instrumentation and Measurement, vol. 44, No. 3, Jun. 1995, pp. 743-746.

Andrews et al., "Hybrid FES Orthosis Incorporating Closed Loop Control and Sensory Feedback," Journal of Biomedical Engineering, vol. 10, Apr. 1988, pp. 189-195.

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

Bar et al., "Adaptive Microcomputer Control of an Artificial Knee in Level Walking," Journal of Biomechanical Engineering, vol. 5, Apr. 1983, pp. 145-150.

Blaya, "Force-Controllable Ankle Foot Orthosis (AFO) to Assist Drop Foot Gait," Massachusetts Institute of Technology, Thesis, Feb. 2003 (believed to be catalogued on or after Jul. 8, 2003) in 97 pages.

Dai et al., "Application of Tilt Sensors in Functional Electrical Stimulation," IEEE Transactions on Rehabilitation Engineering, vol. 4, No. 2, Jun. 1996, pp. 63-72.

Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.

Foerster et al., "Detection of Posture and Motion by Accelerometry: A Validation Study in Ambulatory Monitoring," Computers in Human Behavior, vol. 15, 1999, pp. 571-583.

Frank et al., "Reliable Real-Time Recognition of Motion Related Human Activities Using MEMS Inertial Sensors," 2010, http://www.xsens.com/images/stories/PDF/Activity_Recognition_Final_ION_2010_Paper.pdf.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Heyn et al., "The Kinematics of the Swing Phase Obtained From Accelerometer and Gyroscope Measurements," 18th Annual International Conference of the IEEE Engineering in Medicine and Biology Society, Amsterdam 1996, pp. 463-464.

Jonic et al., "Three Machine Learning Techniques for Automatic Determination of Rules to Control Locomotion," IEEE, Transactions on Biomedical Engineering, vol. 46, No. 3, Mar. 1999, pp. 300-310.

Kirkwood et al., "Automatic Detection of Gait Events: A Case Study Using Inductive Learning Techniques," Journal of Biomedical Engineering, vol. 11, Nov. 1989, pp. 511-516.

Kostov et al., "Machine Learning in Control of Functional Electrical Stimulation Systems for Locomotion," IEEE Transactions on Biomedical Engineering, vol. 42, No. 6, Jun. 1995, pp. 541-551.

Lee et al., "Activity and Location Recognition Using Wearable Sensors," Pervasive Computing, Jul.-Sep. 2002, pp. 24-32.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12.

Martin, C.W., Otto Bock C-leg: A Review of Its Effectiveness, WCB Evidence Based Group, Nov. 27, 2003.

Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.

Moe-Nilssen, R.; "A New Method for Evaluating Motor Control in Gait Under Real-Life Environmental Conditions. Part 1: The Instrument" Clinical Biomechanics, vol. 13, 1998, pp. 320-327.

Moe-Nilssen, R.; "A New Method for Evaluating Motor Control in Gait Under Real-Life Environmental Conditions. Part 2: Gait Analysis" Clinical Biomechanics, vol. 13, 1998, pp. 328-335.

Nakagawa, Akio; "Intelligent Knee Mechanism and the Possibility to Apply the Principle to the Other Joints," Proceedings of the 20th Annual International Conference of the IEEE Engineering in Medicine and Biology Society, vol. 20, No. 5, Dec. 1998, pp. 2282-2287.

Petrofsky et al., "Feedback Control System for Walking in Man," Computers in Biology and Medicine, vol. 14, No. 2, pp. 135-149, 1984.

Popovic et al., "Control Aspects of Active Above-Knee Prosthesis," International Journal of Man-Machine Studies, vol. 35, No. 6, Dec. 1991, pp. 751-767.

Reitman et al., "Gait Analysis in Prosthetics: Opinions, Ideas, and Conclusions," Prosthetics and Orthotics International, vol. 26, 2002, 50-57.

Robinson et al., "Series Elastic Actuator Development for a Biomimetic Walking Robot," MIT Leg Laboratory, 1999, pp. 1-8.

Sekine et al., "Classification of Waist-Acceleration Signals in a Continuous Walking Record," Medical Engineering & Physics, 2000, pp. 285-291.

Smidt et al., "An Automated Accelerometry System for Gait Analysis," Journal of Biomechanics, vol. 10, 1977, pp. 367-375.

Tomović et al., "A Finite State Approach to the Synthesis of Bioengineering Control Systems," IEEE Transactions of Human Factors in Electronics, vol. HFE-7, No. 2, Jun. 1966, pp. 65-69.

Tong et al., "A Practical Gait Analysis System Using Gyroscopes," Medical Engineering and Physics, vol. 21, 1999, pp. 87-94.

Tong et al., "Virtual Artificial Sensor Technique for Functional Electrical Stimulation," Medical Engineering & Physics, vol. 20, 1998, pp. 458-468.

Townsend et al., "Biomechanics and Modeling of Bipedal Climbing and Descending," Journal of Biomechanics, vol. 9, No. 4, 1976, pp. 227-239.

Van Der Kooij et al., "A Multisensory Integration Model of Human Stance Control," Biological Cybernetics, vol. 80, pp. 299-308, 1998.

Veltink et al., "Detection of Static and Dynamic Activities using Uniaxial Accelerometers," IEEE Transactions on Rehabilitation Engineering, vol. 4, No. 4, Dec. 1996, pp. 375-385.

Veltink et al., "The Feasibility of Posture and Movement Detection by Accelerometry," 15th Annual International Conference of the IEEE Engineering in Medicine and Biology Society, Oct. 28-31, 1993, San Diego, California, pp. 1230-1231.

Willemsen et al., "Real-Time Gait Assessment Utilizing a New Way of Accelerometry," Journal of Biomechanics, vol. 23, No. 8, 1990. pp. 859-863.

(56) References Cited

OTHER PUBLICATIONS

Woodward et al., "Skeletal Accelerations Measured During Different Exercises," Proceedings of the Institution of Mechanical Engineers, Part H, Journal of Engineering in Medicine, vol. 207, No. 2, Jun. 1993, pp. 79-85.
Sigurdsson et al., "12th Nordic Baltic Conference on Biomedical Engineering and Medical Physics," Proceeding of the International Federation for Medical & Biological Engineering, Jun. 18-22, 2002, Reykjavik, Iceland, pp. 6.
Bonivento et al., "Automatic Tuning of Myoelectric Prostheses", Journal of Rehabilitation Research and Development, Jul. 1998, vol. 35, No. 3, pp. 294-304.
International Preliminary Report on Patentability and Written Opinion in PCT Application No. PCT/US2014/22013, dated Sep. 24, 2015.
Michael, John W., M.Ed., "Upper Limb Powered Components and Controls: Current Concepts", Clinical Prosthetics and Orthotics, 1986, vol. 10, No. 2, pp. 66-77.
Official Communication in European Application No. 14773653.2, dated Oct. 31, 2016.

* cited by examiner

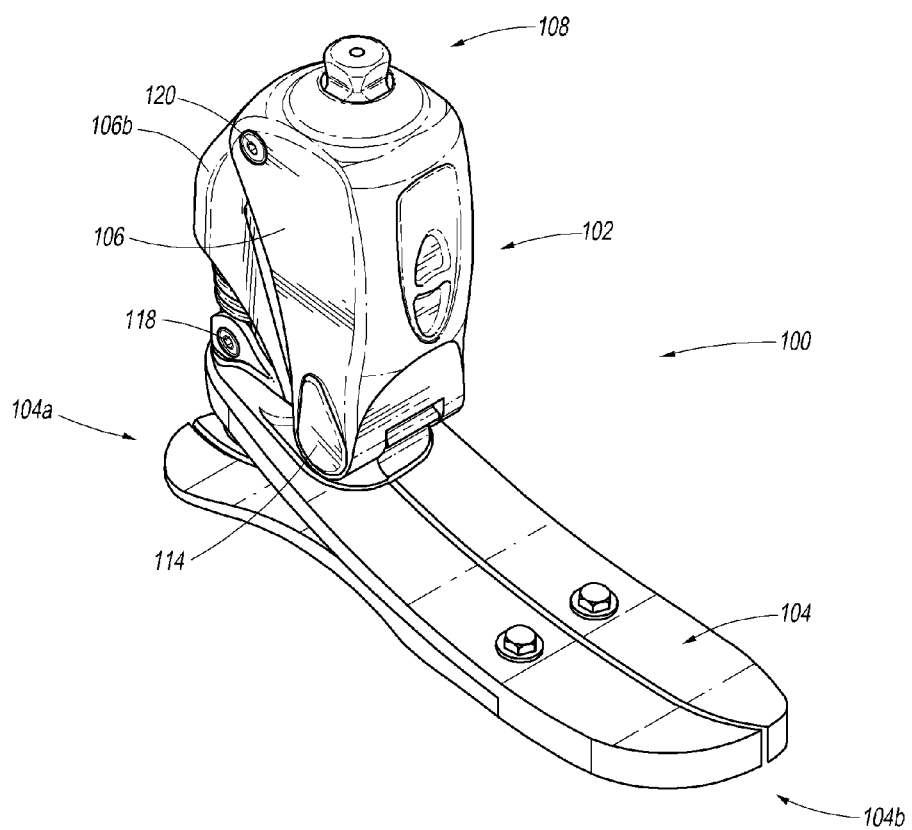
FIG. IA

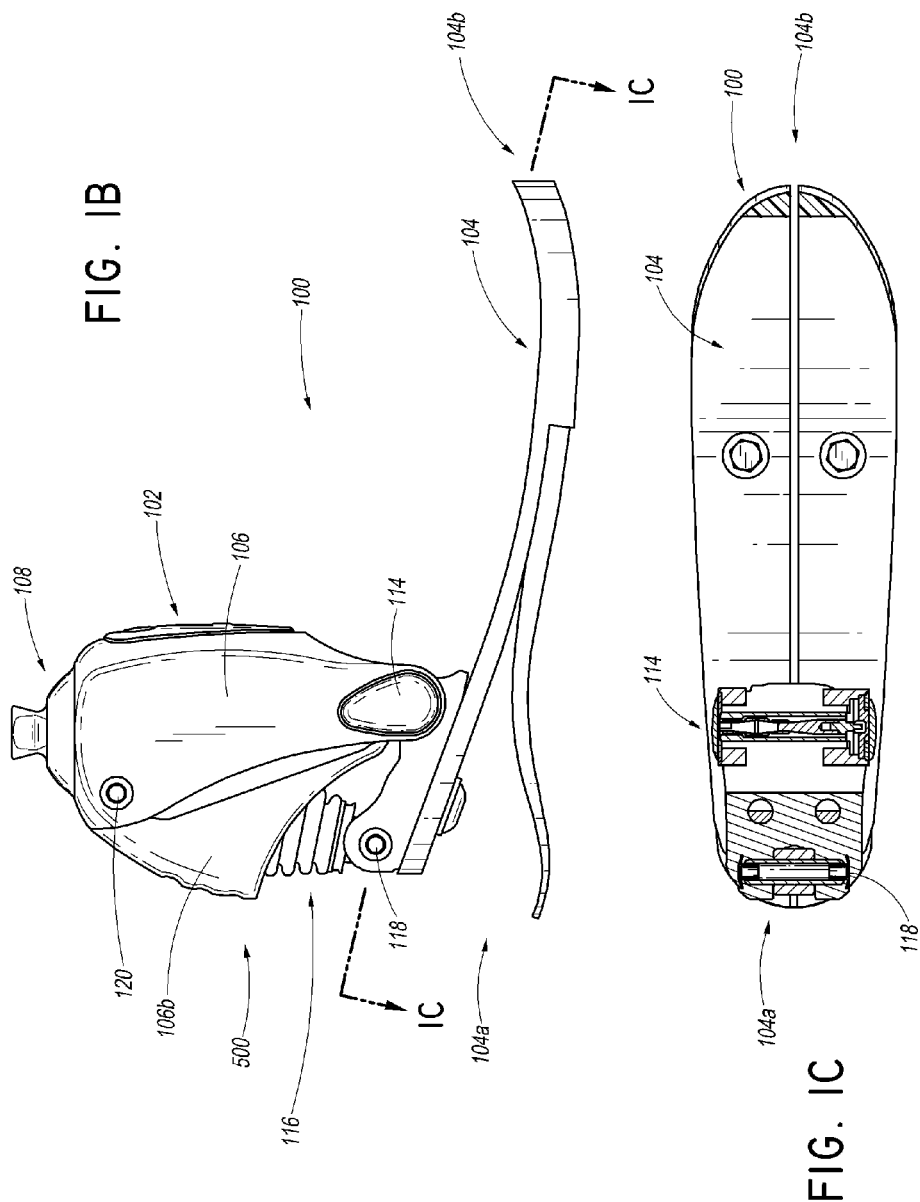

PROSTHETIC ANKLE AND METHOD OF CONTROLLING SAME BASED ON ADAPTATION TO SPEED

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority benefit of U.S. Provisional Application No. 61/785,248, filed Mar. 14, 2013, the entirety of which is hereby incorporated by reference herein and should be considered a part of this specification.

BACKGROUND

Field

The present disclosure relates to prosthetic devices including control systems and methods for controlling prosthetic devices.

Description of the Related Art

Various types of prosthetic devices are available as artificial substitutes for a missing body part, such as an arm or leg. Prosthetic joints are also available as substitutes for human joints, such as an ankle or knee. Electronically controlled prosthetic devices, or "mechatronic" devices, can provide safer and more natural movement. Improvements to control systems for such mechatronic devices could advantageously allow the devices to more closely approximate the movement of natural joints and provide users with a greater range of motion and greater stability.

SUMMARY

The present disclosure provides prosthetic devices and methods for controlling prosthetic devices, for example, prosthetic joints. The methods described herein can be used to control prosthetic devices of various types and structures. For example, the methods can be used to control actuated joints that are active or passive. The methods described herein can also be used to control prosthetic devices operatively coupled to and used by both transfemoral and transtibial amputee users.

Some embodiments of the present disclosure provide methods of controlling a prosthetic ankle device that includes a foot unit and a lower limb member configured to move relative to the foot unit and defines an angle between the foot unit and lower limb member. In one embodiment, a method of controlling the prosthetic ankle device includes operating the prosthetic ankle device using a neutral ankle angle at a gait speed less than a first threshold speed. The method further includes operating the prosthetic ankle device using a speed adaptive ankle angle at a gait speed at or above the first threshold speed and below a second threshold speed. The speed adaptive ankle angle is less than the neutral ankle angle so that the prosthetic ankle device is relatively more dorsiflexed than when the prosthetic ankle device is operating using the neutral ankle angle. At a gait speed at or above the second threshold speed, the method includes operating the prosthetic ankle device using a speed adaptive ankle angle that is more than the neutral ankle angle. The prosthetic ankle device is therefore relatively more plantarflexed than when the prosthetic ankle device is operating using the neutral ankle angle.

In some embodiments, at a gait speed at or above the first threshold speed, the speed adaptive ankle angle increases as the gait speed increases. The speed adaptive ankle angle used to operate the prosthetic device can also increase as the gait speed increases at or above the second threshold speed. In some embodiments, at or above a third threshold speed, the speed adaptive ankle angle remains constant as gait speed increases.

In some embodiments of the present disclosure, a prosthetic system includes a prosthetic ankle device and a controller. The prosthetic ankle device includes a foot unit and a lower limb member configured to move relative to the foot unit and defines an angle between the foot unit and lower limb member. The controller is configured to operate the prosthetic ankle device using a neutral ankle angle at a gait speed less than a first threshold speed. At a gait speed at or above the first threshold speed and below a second threshold speed, the controller is configured to operate the prosthetic ankle device using a speed adaptive ankle angle that is less than the neutral ankle angle so that the prosthetic ankle device is relatively more dorsiflexed than when the prosthetic ankle device is operating using the neutral ankle angle. At a gait speed at or above the second threshold speed, the controller is configured to operate the prosthetic ankle device using a speed adaptive ankle angle that is more than the neutral ankle angle so that the prosthetic ankle device is relatively more plantarflexed than when the prosthetic ankle device is operating using the neutral ankle angle.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 1A illustrates a perspective view of an example embodiment of a prosthetic ankle device;

FIG. 1B illustrates a side view of the prosthetic ankle device of FIG. 1A;

FIG. 1C illustrates a cross-sectional view of the prosthetic ankle device of FIGS. 1A and 1B;

DETAILED DESCRIPTION

Figure 2:
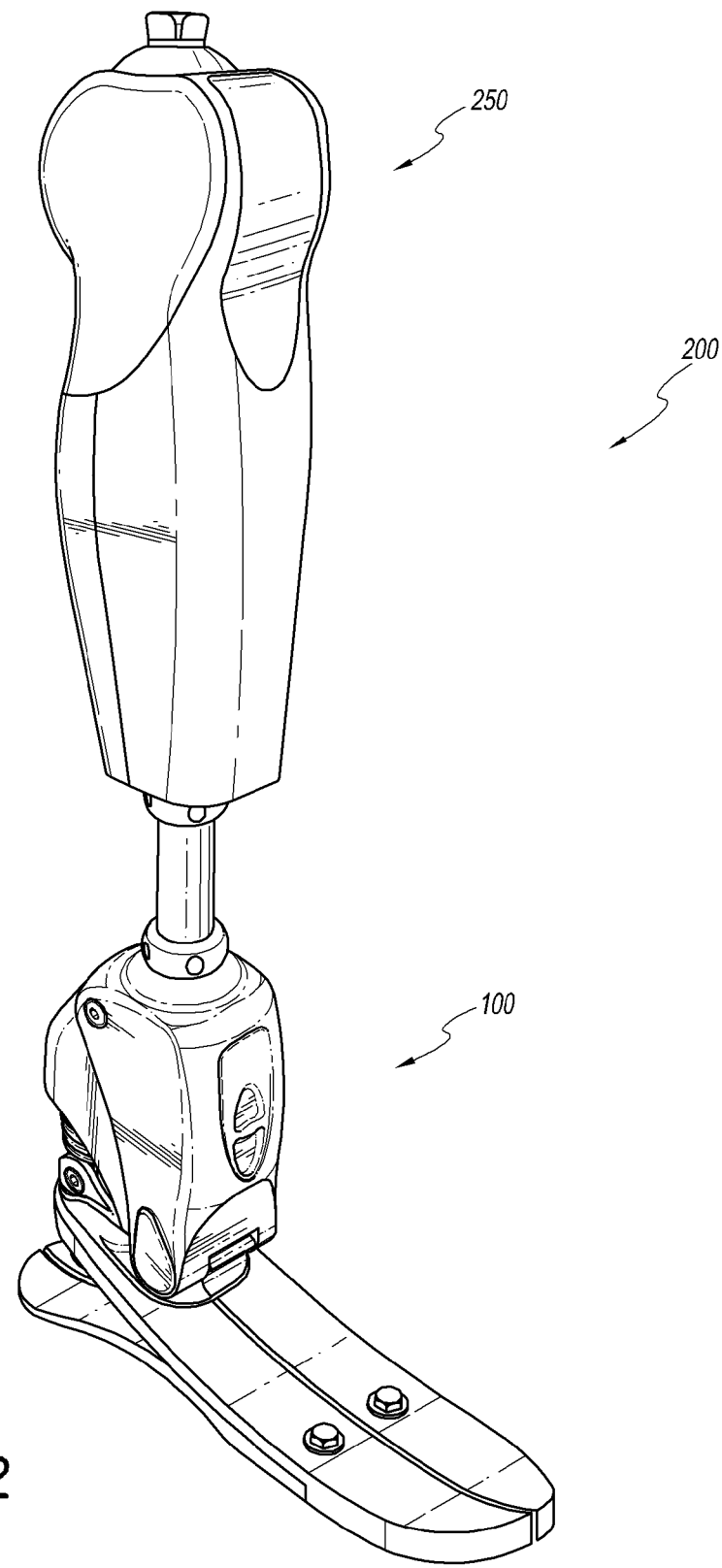
FIG. 2 illustrates a perspective view of an example embodiment of a transfemoral prosthetic device including the prosthetic ankle device of FIGS. 1A-1C and an example embodiment of a prosthetic knee device.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

With reference to FIGS. 1A-1C, an example embodiment of a prosthetic ankle device 100 can include an attachment member, in the form of a lower limb member 102, operatively coupled to a foot unit 104. As used herein, the term "attachment member" is a broad term and is used in its ordinary sense and in a prosthetic foot embodiment relates to, without limitation, any member that attaches either directly or indirectly to the foot unit 104 and is moveable in relation thereto, for example by a pivoting motion, and is used to attach the prosthesis 100 to a stump or intermediate prosthesis. As illustrated, the attachment member may take the form of a lower limb member. In other embodiments, for example an orthotic embodiment, the attachment member may be used to attach to and support a body part, such as with a brace, which also is moveably connected to a second member, such as a foot unit, which would also attach to and support a body part, such as the foot. In one embodiment, the lower limb member 102 is a generally elongated member with a main longitudinal axis that extends in about a tibial direction, that is, a direction that extends generally along the axis of a natural tibia bone. For example, FIGS. 1A and 1B depict the lower limb member 102 as having a generally vertical orientation.

The illustrated lower limb member 102 includes an attachment portion 108. The attachment portion 108 can couple the lower limb member 102 to a pylon or to another prosthetic device, as described below. In other embodiments, the attachment portion 108 can couple the lower limb member to the user's residual limb, e.g., to a socket coupled to the residual limb. In some embodiments, no attachment portion 108 may be provided at all, such as when the lower limb member is directly integrated with a prosthetic knee. The lower limb member 102 can be movably, e.g., pivotally, attached to the foot unit 104 to form a pivoting ankle joint. The prosthetic ankle device 100 can therefore provide for heel height adjustability. In some embodiments, a prosthetist or user can determine or calibrate a neutral ankle angle for the prosthetic device 100. The neutral ankle angle can be an angle between the foot unit 104 and lower limb member 102 that is suited for the particular user when standing still on level ground.

The foot unit 104 can include various types of prosthetic or orthotic feet. In some embodiments, the foot unit 104 includes a foot or upper plate and/or a heel or lower plate extending between a heel portion 104a of the foot 104 and a toe portion 104b of the foot 104. In some embodiments, the foot unit 104 can include such features as shock absorption and/or a split toe configuration, which can facilitate movement on uneven terrain. The foot unit 104 can further include a foot cover or cosmesis.

In the illustrated embodiment, the lower limb member 102 includes a cover 106 that houses and/or protects the inner components of the lower limb member 102. In some embodiments, the lower limb member 102 also includes a rear cover 106b. In some embodiments, the cover 106 can be rounded or shaped in the form of a natural human leg. In the illustrated embodiment, a lower end of the lower limb member 102 is coupled to the foot unit 104 at a pivot assembly 114. The pivot assembly 114 allows for angular movement of the foot unit 104 with respect to the lower limb member 102. For example, in one embodiment, the pivot assembly 114 comprises at least one pivot pin. In other embodiments, the pivot assembly 114 comprises a hinge, a multi-axial configuration, a polycentric configuration, combinations of the same or the like. In some embodiments, the pivot assembly 114 is located on a portion of the foot unit 104 that is near a natural ankle location of the foot unit 104. The pivot assembly 114 can be bolted or releasably connected to the foot unit 104.

In some embodiments, the prosthesis 100 includes an actuator 116 that controls, adjusts, or otherwise affects the ankle angle, or angle between the foot unit 104 and the lower limb member 102. The actuator 116 can be active or passive. In the illustrated embodiment, a lower end of the actuator 116 is coupled to the foot unit 104 at a first attachment point 118, and an upper end of the actuator 116 is coupled to the lower limb member 102 at a second attachment point 120. Linear motion (or extension and contraction) of the actuator 116 actively adjusts the ankle angle between the foot unit 104 and the lower limb member 102. The actuator 116 can include, for example, a double-screw motor, single-screw motor, piston cylinder-type structure, servomotor, stepper motor, rotary motor, spring, fluid actuator, or the like. In other embodiments, the actuator 116 comprises a passive actuator, for example a hydraulic or pneumatic actuator. The actuator can provide damping to control or affect the ankle angle. Additional details regarding prosthetic ankle devices and actuators, among other details that may be combined, added or interchanged with details described herein, can be found in U.S. Pat. Nos. 7,431,737; 7,896,927; and 7,637,959, the entirety of each of which is hereby incorporated by reference herein, and in U.S. Pat. No. 8,057,550, a copy of which is included herein as Appendix A and the entirety of which is hereby incorporated by reference herein.

Figure 3:
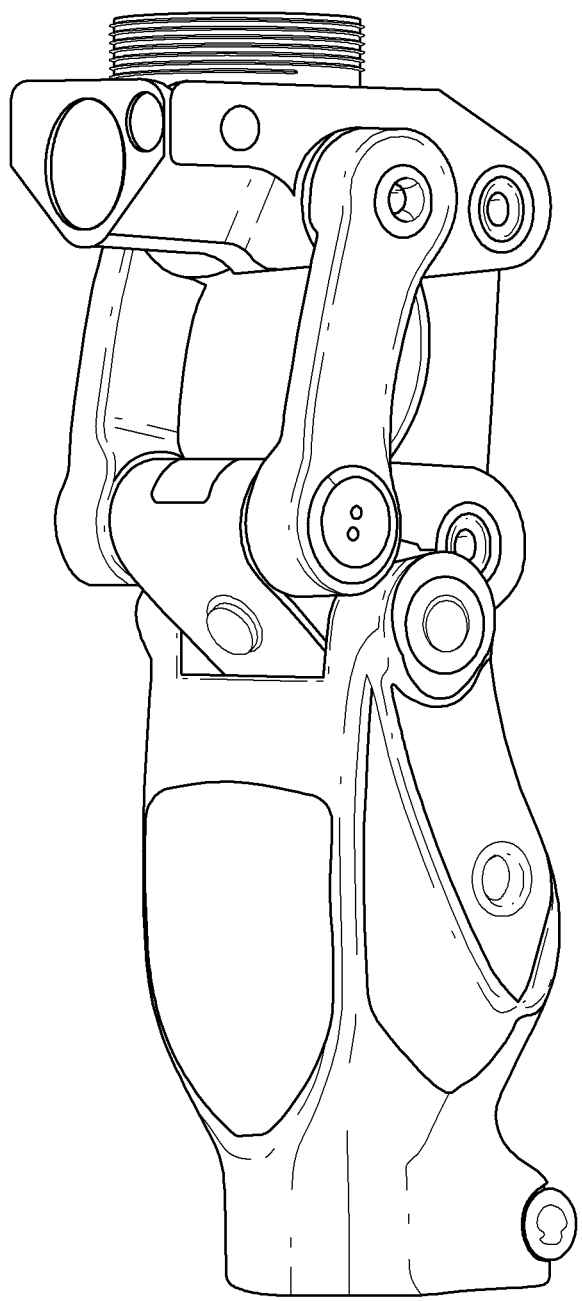
FIGS. 3 and 4 illustrate example embodiments of prosthetic knee devices.
Figure 4:
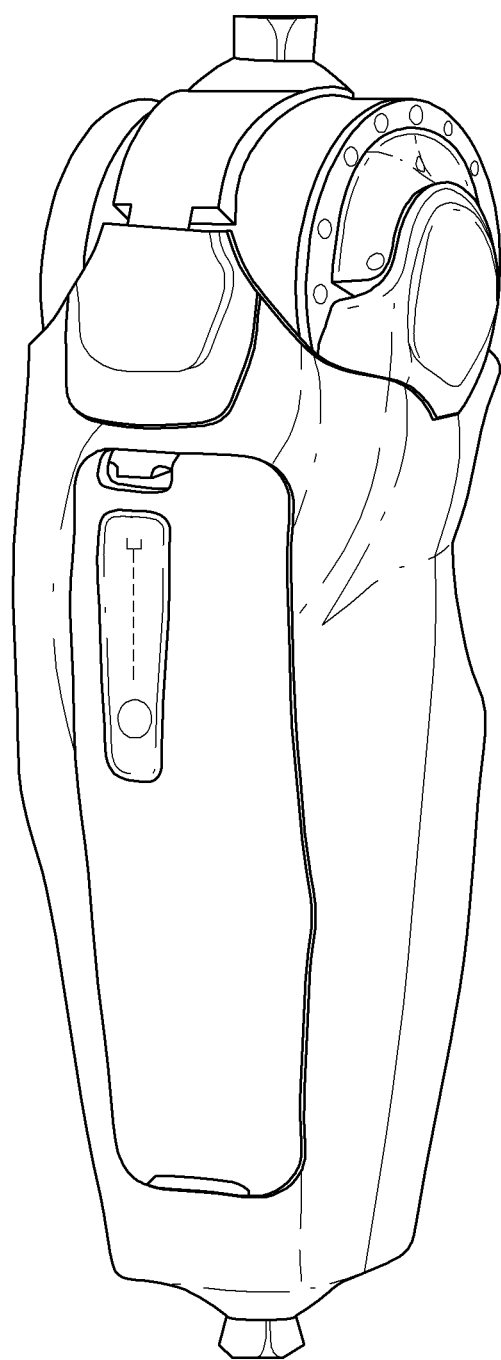

Whereas a trans-tibial amputee may only need a prosthetic ankle device, a transfemoral amputee may also need a prosthetic knee joint. Various types of prosthetic knees, including mechanical knees and active or passive actuated knees, can be used in combination with the prosthetic ankle device 100. For example, FIG. 2 illustrates a transfemoral prosthetic device 200 including the prosthetic ankle device 100 in combination with an example embodiment of a prosthetic knee device 250. Other example prosthetic knees are shown in FIGS. 3 and 4. Various prosthetic knees, and other features that may be combined, added or interchanged with details described herein, are described in U.S. Pat. Nos. 5,314,498; RE42,903; and 7,736,394, and U.S. Patent Publication No. 2009/0299480, the entireties of which are hereby incorporated by reference herein. It will be appreciated that although some embodiments of a prosthetic device encompassed by this disclosure may include discrete a prosthetic ankle device and a discrete prosthetic knee device coupled together, as shown in FIG. 2, other embodiments of the prosthetic device may have both a prosthetic ankle portion and a prosthetic knee portion integrated together and forming a single prosthesis.

Figure 5:
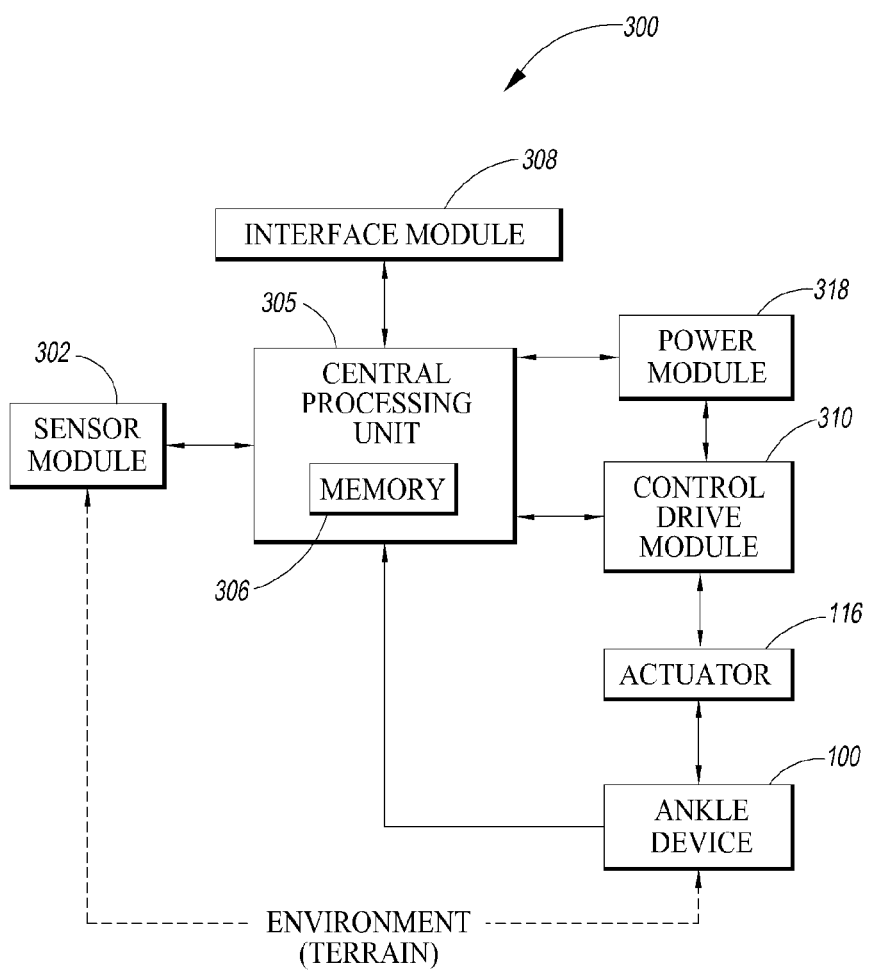
FIG. 5 illustrates a block diagram of an example embodiment of a control system for a prosthetic device.

The prosthetic ankle device 100 can include a control system 300 to control operation of the actuator 116, for example as shown in the block diagram of FIG. 5. In some embodiments, the prosthetic ankle 100 and a knee used in combination with the ankle 100 can be controlled by a single control system 300. The control system 300 can include any or all of: at least one sensor module 302; the prosthetic ankle device 100; a central processing unit ("CPU") or controller 305; a memory 306; an interface module 308; a control drive module 310; actuator 116; and a power module 318. The control system 300 can process data received from the sensor module 302 with the CPU 305. The CPU 305 communicates with the control drive module 310 to control operation of the actuator 116. The CPU 305 can also receive commands from a user and/or other device through the interface module 308.

In some embodiments, the sensor module 302 of the control system 300 can be used to measure one or more variables relating to the prosthetic ankle device 100. The sensor module 302 can include one or more sensors of various types located on the prosthetic ankle device 100 or elsewhere, for example, the user's sound limb or residual limb. For example, the sensor module 302 can include one or more accelerometers, for example, three accelerometers to measure acceleration of the prosthetic ankle device 100 in three substantially mutually perpendicular axes. Additionally or alternatively, the sensor module 302 can include, for example, one or more gyroscopes configured to measure angular speed, plantar pressure sensors configured to measure plantar pressure of the foot unit 104, kinematic sensors, load sensors, flex sensors, myoelectric sensors, and/or other sensors as desired or required.

The sensors can be used to measure one or more variables and/or obtain information relating to, for example, one or more of: the position of the prosthetic ankle device 100 with respect to the ground; the inclination angle of the prosthetic ankle device 100; the direction of gravity with respect to the prosthetic ankle device 100; and the like. In some embodiments, the sensors can be used to measure one or more variables relating to or indicative of the gait cycle of the user, for example to detect or determine heel strike, mid stance, late stance, toe off, and/or swing. The one or more sensors can also or alternatively be used to measure one or more variables indicative of various gait patterns and/or events. For example, one or more sensors can measure one or more variables used to detect or determine when the user is in a standing or stopped position, walking on level ground, walking on inclines and/or declines, ascending and/or descending stairs, sitting, or the like. In some embodiments, one or more sensors are capable of directly measuring or detecting a particular position, movement, state, condition, or the like of the prosthetic ankle device 100. In some embodiments, one or more sensors measure one or more variables relating to or indicative of a particular position, movement, state, condition, or the like and provide data to the controller 305, which can process the data to calculate or determine the position, movement, state, condition, or the like.

In some embodiments, the sensor module 302 can be used to measure one or more variables indicative of the user's relative or absolute gait speed. In some embodiments, the sensor module 302 includes one or more sensors that directly measure or determine absolute speed in units of distance per time, e.g., meters/second. Examples of such sensors are available from Dynastream Innovations, Inc. In some embodiments, the controller 305 calculates or determines relative or absolute gait speed using data provided by one or more sensors. For example, the controller 305 may receive from one or more sensors or calculate or determine the duration of the stance phase of the gait cycle and/or the cadence of the user's gait (strides per unit of time). The controller 305 can compare these values to experimental data (for example the particular user's normal stance duration or cadence as determined, measured, and/or recorded during a training or set-up session), a look-up table, or the like to determine whether the user is walking relatively slowly, relatively fast, or at a normal speed or pace. For example, if the stance phase is shorter than the user's normal stance phase, the controller 305 can determine that the user is walking relatively fast.

Figure 6:
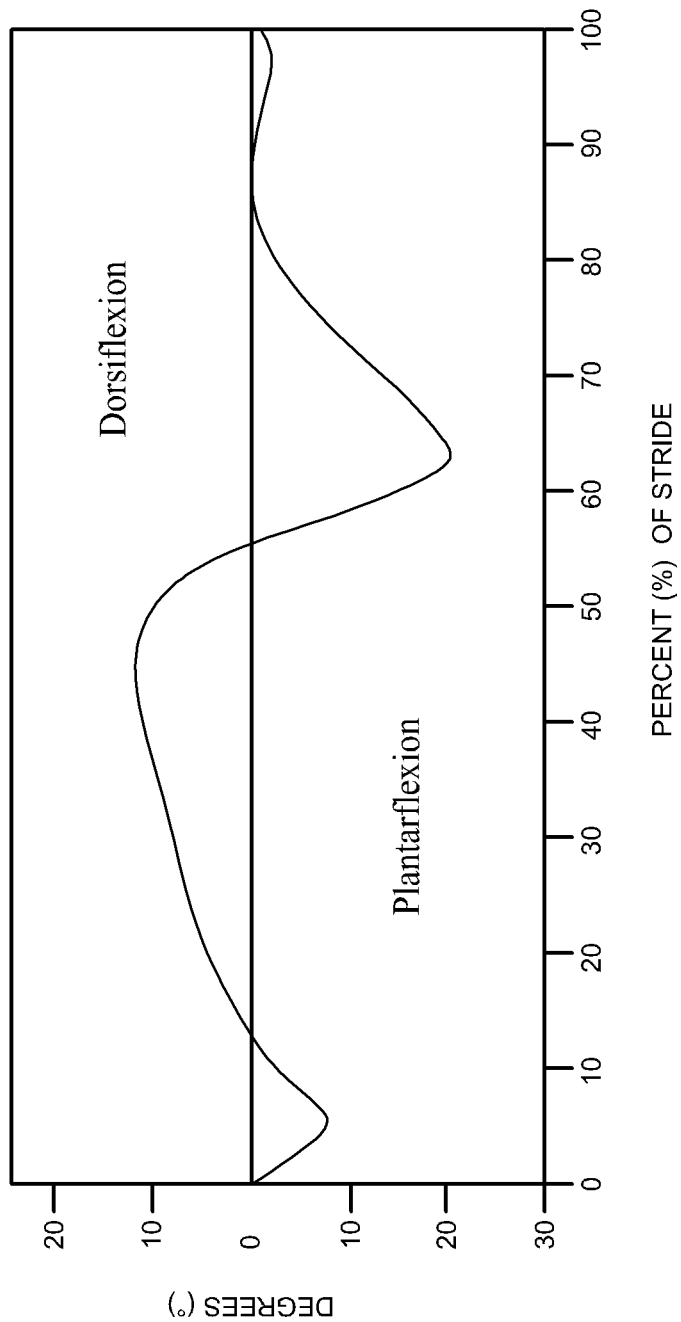
FIG. 6 illustrates a graph depicting the range of ankle motion of an example embodiment of a prosthetic ankle device during one full stride on a level surface.

The prosthetic ankle device 100 can be configured to adjust for various stages of the user's gait cycle, as well as various gait patterns or events, for example, walking on level ground, walking on inclines or declines, or ascending or descending stairs, etc. FIG. 6 illustrates a graph depicting a possible range of motion of an embodiment of the prosthetic ankle device 100 during one full stride on a level surface. As shown, the x-axis represents various points during one full stride of a user (i.e., 0 to 100 percent of the stride). The y-axis represents the ankle angle of the prosthetic ankle device 100 relative to the neutral ankle angle. During one full stride, the ankle angle can vary from about 20° plantarflexion (i.e., neutral ankle angle +20°) to about 10° dorsiflexion (i.e., neutral ankle angle −10°). In some embodiments, the prosthetic ankle device 100 can be configured to provide for toe lift, or relative dorsiflexion, during a swing phase of the gait cycle. This can advantageously provide for toe clearance during swing so that the toe does not catch on the walking surface and cause the user to stumble. The prosthetic ankle device 100 can be configured to adjust for walking on inclines or declines by decreasing or increasing the ankle angle, respectively, to an adjusted ankle angle. In some embodiments, the prosthetic ankle device 100 remains locked at the adjusted ankle angle over the course of the gait cycle. In some embodiments, the prosthetic ankle device 100 is configured to adjust or allow adjustments for various stages of the user's gait cycle and/or gait patterns or events using or based on the adjusted ankle angle. Additional details on adjusting for inclines, declines, stages of the gait cycle, and/or gait patterns and events can be found in U.S. Pat. No. 7,637,959, which has been incorporated by reference herein.

In some embodiments, the prosthetic ankle device 100 can be configured to adapt to different gait speeds of the user. For example, the prosthetic ankle device 100 can provide for relatively more dorsiflexion at relatively slower gait speeds and relatively more plantarflexion at relatively faster gait speeds. Providing relatively more dorsiflexion can inhibit or reduce heel rise during mid to late stance, which can cause a shortened stride and reduced plantarflexion or push-off at toe off, as is more common at slower gait speeds in healthy individuals. Providing relatively more plantarflexion can conversely provide increased plantarflexion or push-off at toe off and a lengthened stride, as is more common at faster gait speeds in healthy individuals.

The controller 305 can be configured to operate the prosthetic ankle device 100 using different ankle angles depending on the user's gait speed, for example, depending on whether the user's gait speed is below, at, or above certain threshold speeds or whether the user is walking relatively slowly or relatively fast. As used herein, the terms "operate" and "operating" are broad terms and include, without limitation, adjusting, moving, controlling, functioning, causing to function or behave in a particular manner, effecting a particular state or condition, and/or providing in a particular state or condition. For example, the controller 305 can be considered to be operating the prosthetic ankle device 100 anytime a user is wearing the device, regardless of whether the user is moving or whether the ankle angle is changing. In some embodiments, the controller 305 operates the prosthetic ankle device 100 using or based on the neutral ankle angle when the user's gait speed is below a first threshold. At or above the first threshold speed, the controller 305 operates the prosthetic ankle device 100 using a speed adaptive ankle angle. As used herein, the term "speed adaptive ankle angle" is a broad term and can refer to, for example, an initial angle at which a prosthetic ankle device operates at a given speed, and can be an angle at which the prosthetic ankle device is locked over a gait cycle or a baseline angle from which the prosthetic ankle device makes or allows adjustments over a gait cycle or in response to certain conditions.

In some embodiments, when the gait speed is between the first threshold speed and a second threshold speed, inclusive of the first threshold speed, the speed adaptive ankle angle is less than the neutral ankle angle. This means that the prosthetic ankle device 100 is relatively more dorsiflexed compared to when operating using the neutral ankle angle. In some embodiments, when the gait speed is at or above the second threshold speed, the speed adaptive ankle angle is greater or more than the neutral ankle angle so that the prosthetic ankle device 100 is relatively more plantarflexed than when operating using the neutral ankle angle. In some embodiments, the controller 305 can be considered to operate the prosthetic ankle device 100 using a speed adaptive ankle angle that is equal to the neutral ankle angle when the user's gait speed is below the first threshold.

Figure 7:
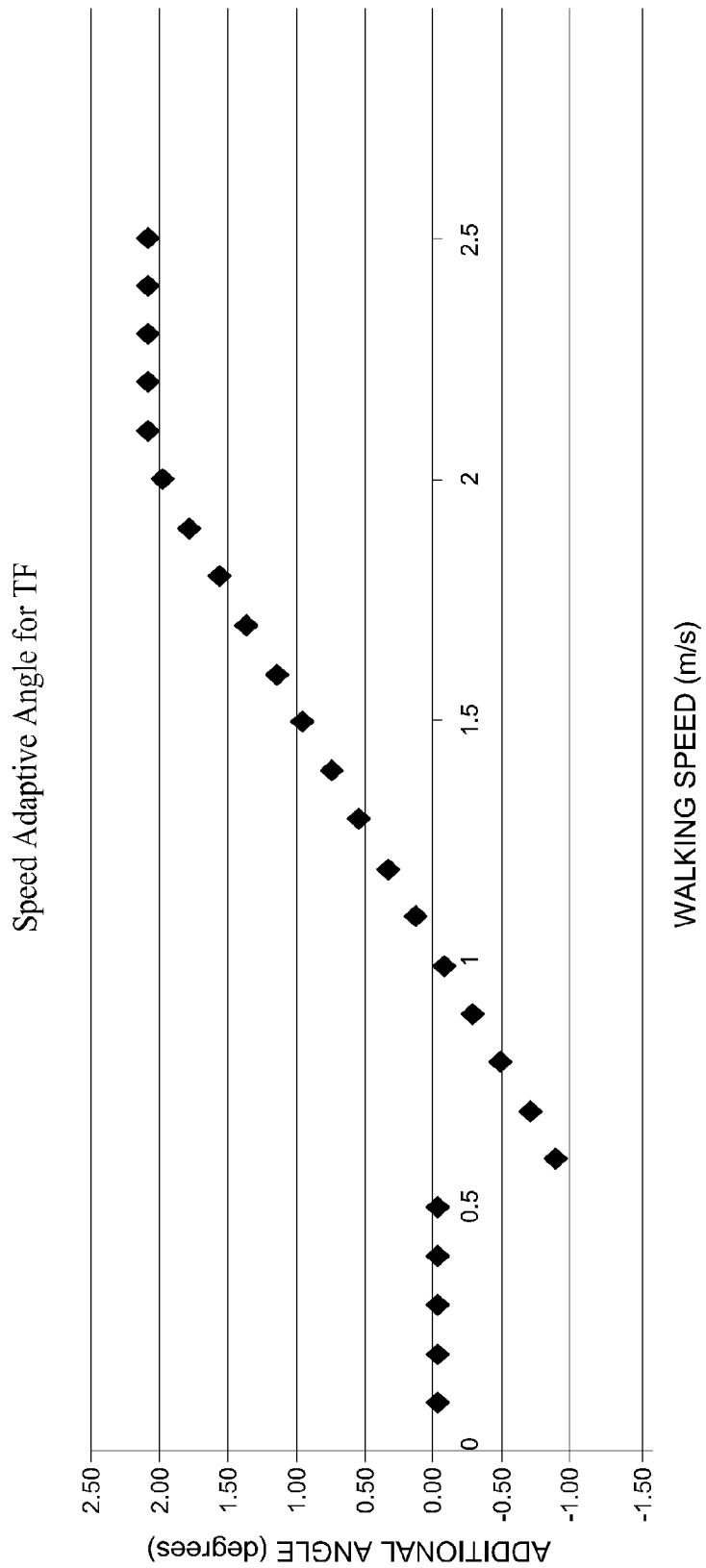
FIG. 7 illustrates a graph of the difference between a speed adaptive ankle angle and a neutral ankle angle at various gait speeds for an example embodiment of a control system for a prosthetic ankle device.

FIG. 7 illustrates a graph of the difference or additional angle between the speed adaptive ankle angle and the neutral ankle angle at various gait speeds according to one embodiment. In the illustrated embodiment, the first threshold speed is 0.55 m/s. The first threshold can be set at 0.55 m/s because below that speed, the user may be considered to be standing still or not moving sufficiently or significantly enough to benefit from a change in the ankle angle. Below this speed, the difference between the speed adaptive ankle angle and the neutral ankle angle is 0°, so the prosthetic ankle device 100 operates using the neutral ankle angle. In some embodiments, the "operating" of the prosthetic ankle device using the neutral ankle angle below the first threshold means that the prosthetic ankle device is simply being worn by a user, and the controller need not be doing anything. At 0.55 m/s, the difference between the speed adaptive ankle angle and the neutral angle is about −1°, so the speed adaptive ankle angle is about 1° less than the neutral ankle angle and the prosthetic ankle device 100 becomes about 1° more dorsiflexed compared to the neutral ankle angle. At the first threshold speed, the ankle angle can substantially instantaneously move to the 1° relatively more dorsiflexed position. Alternatively, the ankle angle can gradually transition to the relatively more dorsiflexed position over a period of time or over a range of gait speeds.

In some embodiments, the difference between the speed adaptive ankle angle and the neutral ankle angle decreases as gait speed increases from the first threshold speed to the second threshold speed. The prosthetic ankle device 100 remains relatively more dorsiflexed than the neutral ankle angle below the second threshold speed, but to a lessening extent as the speed adaptive ankle angle increases as gait speed increases. In the illustrated embodiment, the speed adaptive ankle angle increases linearly as gait speed increases. In the graph of FIG. 7, the second threshold speed is about 1 m/s. At or above the second threshold speed, the difference between the speed adaptive ankle angle and the neutral ankle angle is positive, and the speed adaptive ankle angle is greater than the neutral ankle angle. Therefore, when the user's gait speed reaches the second threshold, the prosthetic ankle device 100 passes through the neutral ankle angle and becomes relatively more plantarflexed compared to the neutral ankle angle. The second threshold can be set at a speed considered or determined to be a transition point between slow and fast walking.

In some embodiments, the difference between the speed adaptive ankle angle and the neutral ankle angle increases as gait speed increases above the second threshold. In the illustrated embodiment, the speed adaptive ankle angle increases linearly as the gait speed increases. The prosthetic ankle device 100 therefore becomes relatively more plantarflexed to a greater degree. In some embodiments, the speed adaptive ankle remains constant when the gait speed reaches a third threshold. In the illustrated embodiment, the third threshold speed is about 2 m/s, and at or above the third threshold speed, the speed adaptive ankle angle remains constant at about 2° greater, i.e., more plantarflexed, than the neutral ankle angle.

The graph of FIG. 7 and the threshold speeds therein are provided as examples only, and other threshold speeds and graph shapes are also possible. For example, in some embodiments, the first threshold speed is 0.65 m/s when the prosthetic ankle device 100 is operatively connected to and used by a transtibial amputee and 0.55 m/s when the prosthetic ankle device 100 is operatively connected to and used by a transfemoral amputee, possibly in combination with a prosthetic knee. It can be beneficial to have a lower first threshold speed for transfemoral amputees because a transfemoral user may have a slower gait speed and more limited movement than a transtibial amputee who still has his or her natural knee. In some embodiments, the threshold speeds are determined experimentally for individual users. In some embodiments, the threshold speeds are set and the user's gait speed is determined in terms of stance phase duration, gait cadence, or the like. In some such embodiments, stance phase duration and/or gait cadence can be less affected by variations in stride lengths among different users than a gait speed measured in, for example, meters/second.

Figure 8:
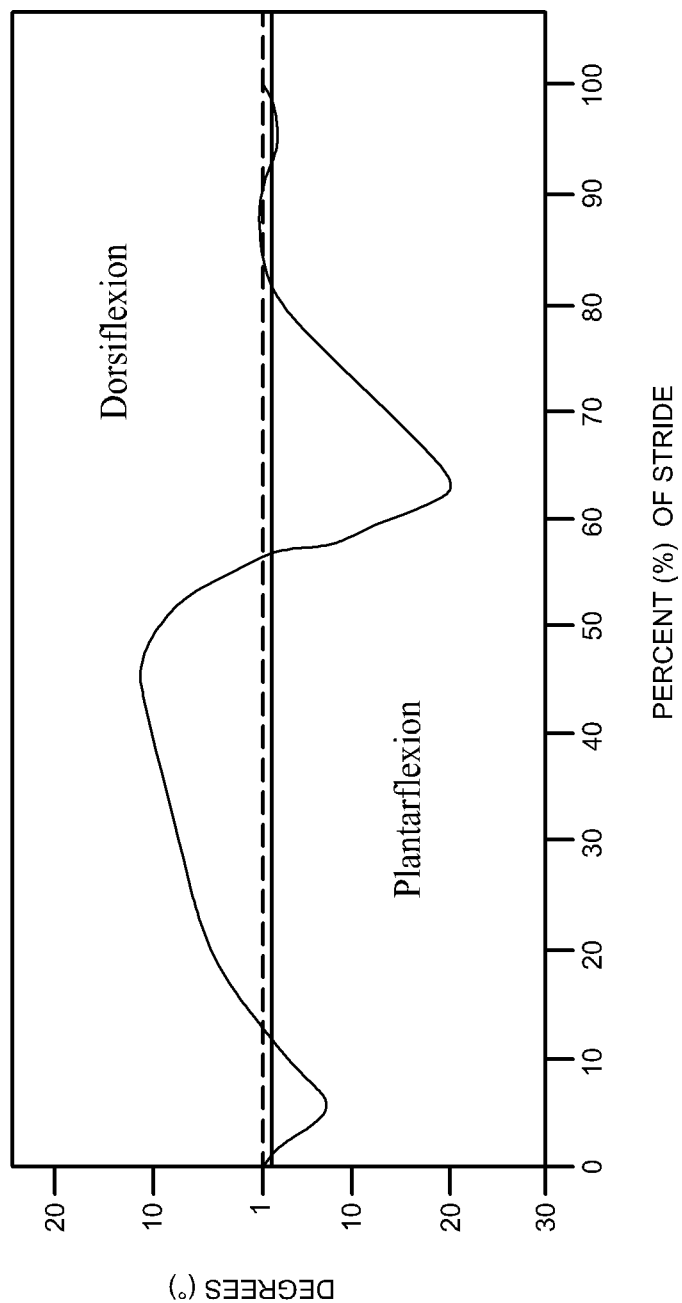
FIG. 8 illustrates a graph depicting the range of ankle motion of an example embodiment of a prosthetic ankle device during one full stride on a level surface at a relatively slower gait speed.
Figure 9:
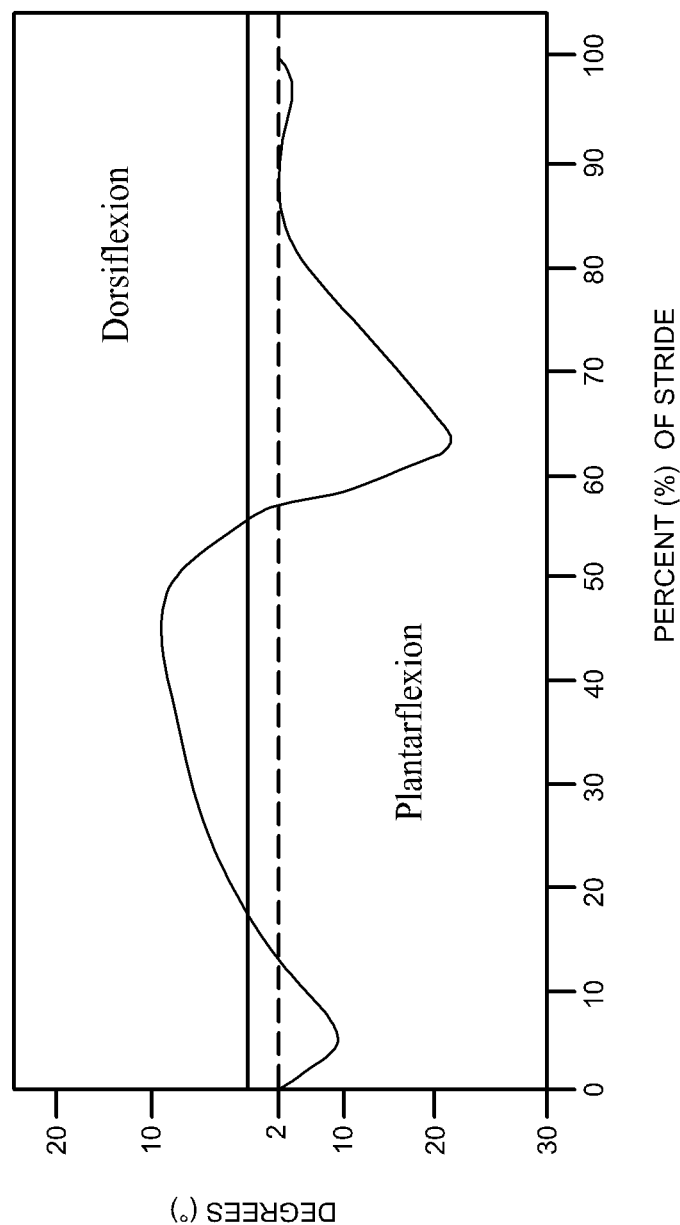
FIG. 9 illustrates a graph depicting the range of ankle motion of an example embodiment of a prosthetic ankle device during one full stride on a level surface at a relatively faster gait speed.

In some embodiments, the prosthetic ankle device 100 maintains or is locked at the speed adaptive ankle angle during part or all of the gait cycle. In some embodiments, the prosthetic ankle device 100 adjusts for or allows for adjustment or movement during certain phases of the gait cycle or certain gait patterns or events as described herein at various gait speeds, but such adjustments are made from, using, or relative to the speed adaptive ankle angle rather than the neutral ankle angle. For example, FIG. 8 illustrates a graph depicting a possible range of motion of an embodiment of the prosthetic ankle device 100 used by a transfemoral amputee during one full stride on a level surface at a gait speed of about 0.55 m/s. FIG. 9 illustrates a graph depicting a possible range of motion of an embodiment of the prosthetic ankle device 100 during one full stride on a level surface at a gait speed of about 2 m/s. For FIG. 8, the speed adaptive ankle angle shifts the entire graph of FIG. 6 by 1° toward dorsiflexion, such that the ankle angle of the prosthetic ankle will adjusted according to the curve of FIG. 8 instead of the curve of FIG. 6 at about 0.55 m/s. Similarly, For FIG. 9, the speed adaptive ankle angle shifts the entire graph of FIG. 6 by 2° toward plantarflexion, such that the ankle angle of the prosthetic ankle will adjusted according to the curve of FIG. 9 instead of the curve of FIG. 6 at about 2 m/s. Thus, whereas in FIG. 6 a prosthetic ankle device 100 is configured to adjust to about 10° of dorsiflexion (−10° from the neutral ankle angle) during the swing phase of the gait cycle to provide for toe clearance, the prosthetic ankle device 100 can provide for about 11° of dorsiflexion (−11° from the neutral ankle angle) at a gait speed of about 0.55 m/s and about 8° of dorsiflexion (−8° from the neutral ankle angle) at a gait speed of about 2 m/s.

In some embodiments, the prosthetic ankle device 100 is configured to adapt to the user being in a standing or stopped position or to certain movements the user may make when in a standing or stopped position. For example, the user may shift his or her weight more to his or her sound leg when standing still. If the user does so, the prosthetic ankle device 100 can be configured to cause or allow a slightly dorsiflexed movement to produce a more natural stance and allow the user to more naturally bend his or her knee. This weight-shifting dorsiflexion feature can be triggered by one or more sensors detecting no movement for a period of time, for example about 10 seconds to about 30 seconds. In some embodiments, the weight-shifting dorsiflexion feature can be triggered by the control system 300 detecting or determining vertical lift of and/or reduced load on the prosthetic ankle device 100 with no forward motion. Sensors on the user's sound leg can also be used to detect or determine increased weight or load with no motion. Once this position is detected, in one embodiment an actuator may be used to actively cause the dorsiflexion movement. In some embodiments, the prosthetic ankle device 100 can be triggered to return to normal operation and/or exit a state of weight-shifting dorsiflexion by the control system 300 detecting or determining a slight vertical lowering of and/or an increased load on the prosthetic ankle device 100, possibly accompanied by acceleration. Sensors on the user's sound leg can also be used to detect or determine decreased weight or load and/or motion.

In some embodiments, the prosthetic ankle device 100 is configured to adapt to other movements the user may make when in a standing or stopped position. For example, the user may shift his or her weight to his or her sound leg and extend the leg including the prosthetic ankle device 100. If the user does so, the prosthetic ankle device 100 can be configured to cause or allow plantarflexion to produce a more natural stance and/or appearance. In some embodiments, the control system 300 determines whether to trigger or allow weight-shifting dorsiflexion or weight-shifting plantarflexion using data from one or more sensors configured to measure one or more variables indicative of the angle of the knee, natural or prosthetic, of the leg including the prosthetic ankle device 100. For example, if the knee angle is less than a threshold angle (meaning the knee is more bent or farther away from complete extension), weight-shifting dorsiflexion is triggered. If the knee angle is equal or greater to the threshold angle (less bent or closer to and up to complete extension), weight-shifting plantarflexion is triggered.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A method of controlling a prosthetic ankle device, comprising:
   providing the prosthetic ankle device, the prosthetic ankle device comprising a foot unit, a lower limb member configured to move relative to the foot unit, the foot unit and lower limb member defining an ankle angle therebetween, and an actuator configured to affect the ankle angle defined between the foot unit and the lower limb member, wherein the actuator comprises an active actuator configured to provide the movement between the foot unit and the lower limb member;
   determining gait speed based on data provided by one or more sensors on the prosthetic ankle device; and
   operating the active actuator of the prosthetic ankle device based on the determined gait speed, wherein:
     at gait speeds less than a first threshold speed, the active actuator of the prosthetic ankle device is operated using a neutral ankle angle curve, wherein the neutral ankle angle curve represents a relationship between percent of completion of a stride of a user of the prosthetic ankle device and number of degrees of the ankle angle, wherein the first threshold speed is greater than zero;
     at gait speeds at or above the first threshold speed and below a second threshold speed and traversed across a level surface, the active actuator of the prosthetic ankle device is operated using a first speed adaptive ankle angle curve that is shifted relative to the neutral ankle angle curve so that, for each percent of completion of the stride corresponding to a same percent completion of the stride on the neutral ankle angle curve, the prosthetic ankle device is more dorsiflexed than when the active actuator of the prosthetic ankle device is operated using the neutral ankle angle curve; and
     at gait speeds at or above the second threshold speed and traversed across the level surface, the active actuator of the prosthetic ankle device is operated using a second speed adaptive ankle angle curve that is shifted relative to the neutral ankle angle curve so that, for each percent of completion of the stride corresponding to a same percent completion of the stride on the neutral ankle angle curve, the prosthetic ankle device is more plantarflexed than when the active actuator of the prosthetic ankle device is operated using the neutral ankle angle curve.

2. The method of claim 1, wherein, at the gait speeds at or above the first threshold speed and below the second threshold speed, points on the first speed adaptive ankle angle curve used to operate the active actuator of the prosthetic ankle device are shifted by smaller amounts relative to the neutral ankle angle curve as the gait speed increases toward the second threshold speed.

3. The method of claim 2, wherein, at the gait speeds at or above the first threshold speed and below the second threshold speed, points on the first speed adaptive ankle angle curve used to operate the active actuator of the prosthetic ankle device are shifted linearly by smaller amounts relative to the neutral ankle angle curve as the gait speed increases toward the second threshold speed.

4. The method of claim 1, wherein, at the gait speeds at or above the second threshold speed and below a third threshold speed, points on the second speed adaptive ankle angle curve used to operate the active actuator of the prosthetic ankle device are shifted by greater amounts relative to the neutral ankle angle curve as the gait speed increases toward the third threshold speed.

5. The method of claim 4, wherein, at the gait speeds at or above the second threshold speed and below the third threshold speed, points on the second speed adaptive ankle angle curve used to operate the active actuator of the prosthetic ankle device are shifted linearly by greater amounts relative to the neutral ankle angle curve as the gait speed increases toward the third threshold speed.

6. The method of claim 1, wherein, at gait speeds at or above a third threshold speed that is greater than the second threshold speed and traversed across the level surface, the active actuator of the prosthetic ankle device is operated using a third speed adaptive ankle angle curve that is shifted relative to the neutral ankle angle curve so that, for each percent of completion of the stride corresponding to a same percent completion of the stride on the neutral ankle angle curve, the prosthetic ankle device is more plantarflexed than when the active actuator of the prosthetic ankle device is operated using the neutral ankle angle curve, and wherein points on the third speed adaptive ankle angle curve are shifted relative to the neutral ankle angle curve by a constant amount as the gait speed increases beyond the third threshold speed.

7. The method of claim 1, wherein the prosthetic ankle device is operatively connected to a transtibial amputee.

8. The method of claim 1, wherein the prosthetic ankle device is operatively connected to a transfemoral amputee.

9. The method of claim 8, wherein the active actuator of the prosthetic ankle device is operated in combination with controlling a prosthetic knee.

10. The method of claim 9, wherein the prosthetic knee is an actuatable prosthetic knee.

11. The method of claim 1, wherein the angle defined between the lower limb member and the foot unit is adjusted based on the gait speed to change to one of the neutral ankle angle and speed adaptive ankle angle curves.

12. A prosthetic system, comprising:
a prosthetic ankle device comprising a foot unit, a lower limb member configured to move relative to the foot unit, the foot unit and lower limb member defining an ankle angle therebetween, and an actuator configured to affect the ankle angle defined between the foot unit and the lower limb member, wherein the actuator comprises an active actuator configured to provide the movement between the foot unit and the lower limb member; and
a controller configured to:
at gait speeds less than a first threshold speed, operate the active actuator of the prosthetic ankle device using a neutral ankle angle curve, wherein the neutral ankle angle curve represents a relationship between percent of completion of a stride of a user of the prosthetic ankle device and number of degrees of the ankle angle, wherein the first threshold speed is greater than zero;
at gait speeds at or above the first threshold speed and below a second threshold speed and traversed across a level surface, operate the active actuator of the prosthetic ankle device using a first speed adaptive ankle angle curve that is shifted relative to the neutral ankle angle curve so that, for each percent of completion of the stride corresponding to a same percent of completion of the stride on the neutral ankle angle curve, the prosthetic ankle device is more dorsiflexed than when the active actuator of the prosthetic ankle device is operated using the neutral ankle angle curve; and
at gait speeds at or above the second threshold speed and traversed across the level surface, operate the active actuator of the prosthetic ankle device using a second speed adaptive ankle angle curve that is shifted relative to the neutral ankle angle curve so that, for each percent of completion of the stride corresponding to a same percent completion of the stride on the neutral ankle angle curve, the prosthetic ankle device is more plantarflexed than when the active actuator of the prosthetic ankle device is operated using the neutral ankle angle curve.

13. The prosthetic system of claim 12, further comprising one or more sensors to measure one or more variables indicative of the user's gait speed.

14. The prosthetic system of claim 12, further comprising a prosthetic knee.

15. The prosthetic system of claim 12, wherein, at the gait speeds at or above the first threshold speed and below the second threshold speed, points on the first speed adaptive ankle angle curve used to operate the active actuator of the prosthetic ankle device are shifted by smaller amounts relative to the neutral ankle angle curve as the gait speed increases toward the second threshold speed.

16. The prosthetic system of claim 15, wherein, at the gait speeds at or above the first threshold speed and below the second threshold speed, points on the first speed adaptive ankle angle curve used to operate the active actuator of the prosthetic ankle device are shifted linearly by smaller amounts relative to the neutral ankle angle curve as the gait speed increases toward the second threshold speed.

17. The prosthetic system of claim 12, wherein, at the gait speeds at or above the second threshold speed and below a third threshold speed, points on the second speed adaptive ankle angle curve used to operate the active actuator of the prosthetic ankle device are shifted by greater amounts relative to the neutral ankle angle curve as the gait speed increases toward the third threshold speed.

18. The prosthetic system of claim 17, wherein, at the gait speeds at or above the second threshold speed and below the third threshold speed, points on the second speed adaptive ankle angle curve used to operate the active actuator of the prosthetic ankle device are shifted linearly by greater amounts relative to the neutral ankle angle curve as the gait speed increases toward the third threshold speed.

19. The prosthetic system of claim 12, wherein, at gait speeds at or above a third threshold speed that is greater than the second threshold speed and traversed across the level surface, the active actuator of the prosthetic ankle device is operated using a third speed adaptive ankle angle curve that is shifted relative to the neutral ankle angle curve so that, for each percent of completion of the stride corresponding to a same percent completion of the stride on the neutral ankle angle curve, the prosthetic ankle device is more plantarflexed than when the active actuator of the prosthetic ankle device is operated using the neutral ankle angle curve, and wherein points on the third speed adaptive ankle angle curve are shifted relative to the neutral ankle angle curve by a constant amount as the gait speed increases beyond the third threshold speed.

20. The prosthetic system of claim 12, wherein the prosthetic ankle device is operatively connected to a transtibial or transfemoral amputee.

21. The prosthetic system of claim 12, further comprising a prosthetic knee, wherein the controller is further configured to control the prosthetic knee.

* * * * *